(12) United States Patent
Vanden Heuvel et al.

(10) Patent No.: US 7,015,249 B1
(45) Date of Patent: Mar. 21, 2006

(54) METHODS AND COMPOSITIONS FOR TREATING DIABETES

(75) Inventors: John P. Vanden Heuvel, Port Matilda, PA (US); Martha A. Belury, Redmond, WA (US); Louise W. Peck, Moscow, ID (US)

(73) Assignees: Purdue Research Foundation, West Lafayette, IN (US); Penn State Research Foundation, University Park, PA (US)

(*) Notice: Subject to any disclaimer, the term of this patent is extended or adjusted under 35 U.S.C. 154(b) by 0 days.

(21) Appl. No.: 09/555,987

(22) PCT Filed: Dec. 11, 1998

(86) PCT No.: PCT/US98/26469

§ 371 (c)(1),
(2), (4) Date: Sep. 11, 2000

(87) PCT Pub. No.: WO99/29317

PCT Pub. Date: Jun. 17, 1999

Related U.S. Application Data (60) Provisional application No. 60/069,567, filed on Dec. 12, 1997.

(51) Int. Cl.
*A61K 31/20* (2006.01)

(52) U.S. Cl. .................................................. 514/560
(58) Field of Classification Search ................. 514/560
See application file for complete search history.

(56) References Cited

U.S. PATENT DOCUMENTS

| | | | |
|---|---|---|---|
| 4,407,821 A | 10/1983 | Mendy | |
| 4,472,432 A | 9/1984 | Iwamura et al. | 424/318 |
| 4,868,212 A | 9/1989 | Horrobin | 514/552 |
| 4,871,768 A | 10/1989 | Bistrian | |
| 5,017,614 A | 5/1991 | Pariza et al. | 514/558 |
| 5,034,415 A | 7/1991 | Rubin | 514/560 |
| 5,070,104 A | 12/1991 | Pariza et al. | 514/549 |
| 5,208,356 A | 5/1993 | Pariza et al. | |
| 5,428,072 A | 6/1995 | Cook et al. | 514/560 |
| 5,430,066 A | 7/1995 | Cook et al. | 514/558 |
| 5,504,114 A | 4/1996 | Cook et al. | 514/558 |
| 5,518,751 A * | 5/1996 | de Boer et al. | |

(Continued)

FOREIGN PATENT DOCUMENTS

EP 0624317 A 11/1994

(Continued)

OTHER PUBLICATIONS

Semenkovich and Heinecke, Diabetes, 1997;46:327-334.*

(Continued)

*Primary Examiner*—San-Ming Hui
(74) *Attorney, Agent, or Firm*—Henry D. Coleman; R. Neil Sudol; William J. Sapone (57) ABSTRACT

Methods of treating diabetes in an animal and food compositions useful for treating diabetes are described. In one aspect of the invention, the method includes treating the animal with a therapeutically effective amount of CLA including 9,11-octadecadienoic acid and 10,12-octadecadienoic acid, isomers thereof, esters thereof, salts thereof or mixtures thereof. In another aspect of the invention, a food composition comprising a food product having a therapeutically effective amount of a purified CLA isomer, including cis,cis-9,11-octadecadienoic acid, trans,cis-10,12-octadecadienoic acid or a mixture of purified cis,trans-9,11-octadecadienoic acid and trans,cis-9,11-octadecadienoic acid is described.

18 Claims, 10 Drawing Sheets

U.S. PATENT DOCUMENTS

| | | | |
|---|---|---|---|
| 5,554,646 A | 9/1996 | Cook et al. | 514/560 |
| 5,585,400 A | 12/1996 | Cook et al. | |
| 5,670,540 A | 9/1997 | Horrobin et al. | 514/549 |
| 5,674,901 A | 10/1997 | Cook et al. | 514/558 |
| 5,760,082 A | 6/1998 | Cook et al. | 514/560 |
| 5,760,083 A | 6/1998 | Cook et al. | 514/560 |
| 5,770,247 A | 6/1998 | Satter et al. | 426/2 |
| 5,804,210 A | 9/1998 | Cook et al. | 424/440 |
| 5,827,897 A | 10/1998 | Ailhaud et al. | 514/725 |
| 6,440,931 B1 | 8/2002 | Remmereit et al. | |

FOREIGN PATENT DOCUMENTS

| | | |
|---|---|---|
| WO | WO9813330 A | 4/1998 |
| ZA | 9603360 A | 8/1996 |

OTHER PUBLICATIONS

Steinhart, Journal of Chemical Education, 1996; 73(12): A302.*

Francisco et al., "Diabetes Mellitus" in Pharmacotherapy: A Pathophysiologic Approach, 2nd ed., 1992, pp. 1121-1127.*

Issemann, I. and Green, S., *Activation of a Member of the Steriod Hormone Receptor Superfamily by Peroxisome Proliferators,* Nature, 347:645-650 (1990).

Belury, M., *Conjugated Dienoic Linoleate: A Polyunsaturated Fatty Acid with Unique Chemoprotective Properties,* Nutrition Rev., 53(4):83-89 (1995).

Khoursheed, M. et al., *Metabolic Effects of Troglitazone on Fat-Induced Insulin Resistance in the Rat,* Metabolism, 44(11):1489-1494 (1995).

Willson, T., et al., *The Structure-Activity Relationship between Peroxisome Proliferator-Activated Receptor γ Agonism and the Antihyperglycemic Activity of Thiazolidinediones,* J. Med. Chem. 39:665-668 (1996).

Matreya, Inc., Conjugated Linoleic Acid (CLA), Lipids and Biochemicals (Apr. 9, 1997).

Belury, M., et al., *Dietary Conjugated Linoleic Acid Induces Peroxisome-specific Enzyme Accumulation and Ornithine Decarboxylase Activity in Mouse Liver,* Nutr. Biochem. 8:579-584 (1997).

Houseknecht, K., et al., *Dietary Conjugated Linoleic Acid Normalizes Impaired Glucose Tolerance in the Zucker Diabetic Fatty fa/fa Rat,* Biochem. and Biophys. Res. Com. 244:678-682 (1998).

Chin Sou F et al., Journal of Nutrition, 124(5): 1994, 694-701.

Salminen et al., (1998), *Dietary trans fatty acids increase conjugated linoleic acid levels in human serum,* Nutr. Biochem. 9:93-98.

Belury et al., (1997), *Protection against cancer and heart disease by CLA: potential mechanisms of action,* Nutrition and Disease Update. 1(2):55-62.

* cited by examiner

METHODS AND COMPOSITIONS FOR TREATING DIABETES

CROSS-REFERENCE TO RELATED APPLICATIONS AND SUPPORT

The present application claims the benefit of U.S. Provisional Patent Application Ser. No. 60/069,567, filed on Dec. 12, 1997, which is hereby incorporated by reference in its entirety.

The invention of the present application was made using support under USDA Grant number 3299. Consequently, the government retains certain rights in the invention.

BACKGROUND OF THE INVENTION

The present invention relates generally to methods of treating diabetes. Specifically, the invention relates to methods of treating diabetes in an animal by administering a therapeutically effective amount of conjugated linoleic acid (CLA). The invention further relates to food compositions including a food product having a therapeutically effective amount of a purified isomer of CLA, such as purified cis,cis-9,11-octadecadienoic acid, purified trans,cis-10,12-octadecadienoic acid or a mixture of purified cis,trans-9,11-octadecadienoic acid and trans,cis-9,11-octadecadienoic acid.

Diabetes is one of the most common metabolic diseases and affects hundreds of millions of individuals worldwide. There are two forms of diabetes mellitus: Type 1 (insulin-dependent) and Type II (non-insulin-dependent). The disease can lead to serious complications, including hyperglycemia, macroangiopathy, microangiopathy, neuropathy, nephropathy and retinopathy. Methods of treating diabetes have included administration of insulin in the case of Type I diabetes and administration of various hypoglycemic agents in the case of Type II diabetes. Many of the known hypoglycemic agents exhibit undesirable side effects and are toxic in certain cases. Accordingly, there is a need for additional methods and compositions for treating diabetes. The present invention addresses this need.

SUMMARY OF THE INVENTION

It has been discovered that administration of CLA is advantageous in the treatment of diabetes mellitus. Accordingly, one preferred embodiment of the invention provides a method of treating diabetes including administering to an animal a therapeutically effective amount of CLA.

In a further aspect of the invention, it has been discovered that purified isomers of CLA can be used to advantage in the treatment of diabetes in animals. The invention thus provides methods involving the administration of purified CLA isomers to animals, alone or in predetermined admixtures, and food or administerable unit dosage forms (e.g., tablets, pills, etc.) containing such isomers or mixtures. In particular, a food composition is provided that includes a food product having a therapeutically effective amount of a purified isomer of CLA, such as cis,cis-9,11-octadienoic acid, trans, cis-10,12-octadecadienoic acid or a mixture of purified cis,trans-9,11-octadecadienoic acid and trans,cis-9,11-octadecadienoic acid.

Other features of the invention involve novel methods for modulating (e.g. increasing) the level of expression of certain genes, e.g. genes involved in regulating the expression of lipid metabolism enzymes and/or in regulating adipocyte differentiation, as illustrated in the Examples herein. The methods include administering to an animal an effective amount of CLA to modulate the gene expression.

It is an object of the invention to provide methods of treating an animal with diabetes by administering CLA.

It is a further object of the invention to provide food compositions that may advantageously be used for the treatment of diabetes mellitus.

These and other objects and advantages of the present invention will be apparent from the descriptions herein.

DESCRIPTION OF THE PREFERRED EMBODIMENTS

For the purposes of promoting an understanding of the principles of the invention, reference will now be made to preferred embodiments and specific language will be used to describe the same. It will nevertheless be understood that no limitation of the scope of the invention is thereby intended, such alterations and further modifications of the invention, and such further applications of the principles of the invention as illustrated herein, being contemplated as would normally occur to one skilled in the art to which the invention relates.

The present invention provides methods of treating diabetes and compositions useful in treating diabetes. In one aspect of the invention diabetes is treated in an animal by administering a therapeutically effective amount of CLA. Administration of CLA advantageously normalizes glucose tolerance in diabetic animals as well as reduces plasma insulin, triglyceride and free fatty acid levels. Although the method is advantageous in treating Type II (non-insulin-dependent) diabetes mellitus, it may also be used to treat Type I (insulin-dependent) diabetes mellitus in conjunction with other treatments therefor as known in the art. In yet another aspect of the invention, methods and compositions are provided which involve the use of purified CLA isomers or purified mixtures of CLA isomers. The compositions may include, and the methods may involve the use of, a therapeutically effective amount of purified cis,cis-9,11-octadecadienoic acid, purified trans,cis-10,12-octadecadienoic acid, a mixture of purified cis,trans-9,11-octadecadienoic acid and trans,cis-9,11-octadecadienoic acid, or another purified isomer of CLA.

In a first aspect of the invention, a method of treating diabetes in an animal is provided that includes administering to the animal a therapeutically effective amount of CLA, including salts thereof, esters thereof (including, for example, monoglycerides, diglycerides and triglycerides) active isomers thereof and mixtures thereof. CLA refers to a group of positional and geometric isomers of linoleic acid (cis,cis-9,12-octadecadienoic acid). The positional isomers include isomers having double bonds at either carbon atoms 9 and 11 or carbon atoms 10 and 12 whereas the geometric isomers include isomers having the cis and/or trans configuration. Thus, there are several possible isomers of CLA, including, but not limited to: cis,cis-9,11-octadecadienoic acid; cis,trans-9,11-octadecadienoic acid; trans,cis-9,11-octadecadienoic acid; trans,trans-9,11-octadecadienoic acid; cis,cis-10,12-octadecadienoic acid; cis,trans-10,12-octadecadienoic acid; trans,cis-10,12-octadecadienoic acid; and trans,trans-10,12-octadecadienoic acid. The cis,trans-9,11 and trans,cis-9,11 isomers have not yet been isolated independently from each other and the literature loosely uses the term cis,trans-9,11-octadecadienoic acid to refer to both the cis,trans-9,11 and the trans,cis-9,11 isomers.

The CLA utilized in the present invention may be prepared using techniques known to the art and literature or may be obtained as a commercial product. CLA may be obtained commercially, for example, from companies such as Pharmanutrients, Inc., Lake Bluff, Ill.; NuChek Prep, Elysian Minn.; and Peak Nutrition, Syracuse, Nebr. However, the CLA sold by NuCheck Prep is preferred. The relative proportions of the isomers may vary in the commercially available CLA. The commercial composition may also include other fatty acids such as linoleic acid as well as other lipids such as straight chain hydrocarbons having polar end groups. For example, the CLA mixture may include other fatty acids known in the art, saturated or unsaturated, or breakdown products of CLA. The commercial composition may also include antioxidants such as vitamin E, butylated hydroxyanisole (BHA) or butylated hydroxytoluene (BHT) CLA may also be synthesized by methods known in the art. For example, CLA may be synthesized from isomerization of linoleic acid utilizing, for example, a radical-generating species and a protein rich in sulfur residues as known in the art and as described in Dormandy T L, Wickens D G, Chem. Phys. Lipids 45:353–64 (1987) which is hereby incorporated by reference in it entirety. As another example, CLA may be synthesized from either linoleic acid or safflower oil by heating the linoleic acid or safflower oil in an inert atmosphere with subsequent acidification and extractions as described in U.S. Pat. No. 5,670,082 to Cook et al. which is hereby incorporated by reference in its entirety. Moreover, specific isomers of CLA, such as the trans,trans 9-11, the cis,cis-9,11 isomer, the cis,trans-9,11 (in combination with the trans,cis-9,11 isomer) and the cis, trans-10,12 isomers can be currently synthesized in pure form by methods known in the art. The salts of CLA are those known in the art, including the sodium and potassium salts.

Linoleic acid used to synthesize CLA, or other fatty acids included in the mixture, may be obtained from plant sources, including soybean, cottonseed, corn, sunflower, safflower, canola and palm oils. Soybean, corn, sunflower and safflower oil are particularly rich in linoleic acid. Linoleic acid may also be obtained from hydrolysis of triglycerides isolated from plant sources by methods known in the art. For example, triglycerides may be obtained from plant sources by solvent extraction of plant biomass using aliphatic solvents. Subsequent additional purification may involve distillation, fractional crystallization, degumming, bleaching and steam stripping. The triglycerides may be hydrogenated as needed. The triglycerides may then be hydrolyzed either by enzymatic (e.g., use of lipase) or chemical methods (e.g., by alkaline hydrolysis) known in the art. Linoleic acid may also be synthesized from petrochemical fatty alcohols. Alternatively, free fatty acids and triglycerides may be obtained from commercial sources, including Cargill, Archer Daniel Midlands and Central Soya.

CLA may also be found in ruminant meats, pasteurized dairy products and processed cheeses. Moreover, the amount of CLA in dairy products may be increased by methods known in the art. For example, the amount of CLA in cow's milk may be increased by feeding to a lactating cow a diet either solely of grass or one which contains about 1% to about 5% by weight of a vegetable oil containing linoleic acid or linolenic acid as described in U.S. Pat. No. 5,770,247 to Satter et al. which is hereby incorporated by reference in its entirety. CLA may also be obtained by enzymatic conversion of linoleic acid as known in the art. For example, CLA may be prepared utilizing the enzyme $W^{11}$-cis,$W^{11}$-transisomerase. The enzyme may be obtained, for example, from rumen bacteria, such as *Butyrivibrio fibrisolvens*. Harmless microorganisms in the intestinal tracts of rats and other monogastric animals may also convert linoleic acid to CLA as described in Chin, S F et al., FASEB J, 6 (1992).

CLA may be administered in various forms. For example, CLA may be administered in tablet form, in a solution or emulsion, or in a capsule. CLA may also be mixed with a pharmaceutically acceptable carrier. In tablet form, a solid carrier may include, for example, lactose, starch, carboxymethyl cellulose, dextrin, calcium phosphate, calcium carbonate, synthetic or natural calcium silicate, magnesium oxide, dry aluminum hydroxide, magnesium stearate, sodium bicarbonate, dry yeast or a combination thereof. In solution, the carrier may be an oil but is preferably sterile water or a sterile saline solution for parenteral administration. CLA may also be administered in forms in which other drugs known in the art are administered.

CLA may be administered in a variety of ways. For example, CLA may be administered parenterally, such as orally, intravenously, rectally, as well as intraperitoneally.

In another feature of the invention, it has been discovered that certain CLA isomers have higher activity. Accordingly, in yet another aspect of the invention, purified CLA isomers may be administered to animals in need thereof and may be added to a food product to form a food composition. The CLA isomers may be added to a food product in any form, such as a powder or in an oil such as corn oil either alone or with another oil, such as coconut oil. One preferred food composition includes CLA predominantly (i.e., greater than 50%) comprised of a mixture of purified cis,trans-9,11-octadecadienoic acid and trans,cis-9,11-octadecadienoic acid. Another beneficial food composition may include a mixture predominantly comprised of cis,cis-9,11-octadecadienoic acid or trans,cis-10,12-octadecadienoic acid. In a further preferred embodiment, the food composition may include a mixture of purified cis,trans-9,11-octadecadienoic acid and trans,cis-9,11-octadecadienoic acid. In this regard, the term "purified" as used herein to refer to a particular CLA isomer or mixture of isomers means a CLA composition containing no more than about 10% by weight of CLA isomers other than those specified. Preferably, the identified isomer or mixture will contain no more than about 5% by weight and more preferably no more than about 3% by weight of the other CLA isomers. In vet other aspects of the invention, the food composition may include purified cis,cis-9,11-octadecadienoic acid, or other purified CLA isomers, including trans,cis-10,12-octadecadienoic acid. In further embodiments, the food composition may include a purified mixture of CLA. For example, CLA may be purified to different extents to produce a purified mixture of CLA including less than all of the CLA isomers. The purified CLA isomers may be included in any food product, including, for example, cereals, meats, eggs, cheeses and other dairy products, vegetables, breads and other flour or bran-based products, and confection products. The CLA isomers may also be added to any consumable liquid but may require various emulsifying agents for dissolution.

The therapeutically effective amount administered will have a beneficial effect on an animal with diabetes. For example, the therapeutically effective amount is desirably sufficient to normalize glucose tolerance in a diabetic animal. Normalization of glucose tolerance can be determined, for example, by a glucose tolerance test as known in the art and as described in the examples below. Moreover, the amount of CLA administered will also preferably be sufficient to reduce blood levels of insulin and/or to reduce the level of circulating free fatty acids or triglycerides. The blood levels of insulin, free fatty acids, and triglycerides are desirably reduced by at least about 5%, more preferably by at least about 20%, and further most preferably by at least about 50%. The amount of CLA administered to an animal with diabetes will vary depending on the age of the animal, the general health of the animal and the severity of their diabetic condition. However, it is expected that an animal being treated for diabetes will usually receive at least about 1 mg CLA/kg body weight/day up to the highest level which is not toxic to the animal. Typically, an animal may receive about 1 mg CLA/kg body weight/day up to about 10,000 mg CLA/kg body weight/day. However, it is expected that relatively low doses of CLA will be sufficient, for instance, falling in the range of about 1 mg CLA/kg body weight/day to about 150 mg CLA/kg body weight/day and more desirably about 10 mg CLA/kg body weight/day to about 50 mg CLA/kg body weight/day. Furthermore, when the CLA is included in a food product, it is advantageous to include an amount of CLA per serving of food product that will provide the preferred amounts of CLA/kg body weight/day discussed above.

In yet another feature of the invention, CLA may be administered to an animal in a composition that releases CLA internally, for example, in the form of an ester of CLA, preferably a triglyceride. In a further preferred embodiment, the triglyceride includes at least one CLA residue in the form of an ester with glycerol and may have other unsaturated or saturated fatty acid residues, but preferably the unsaturated fatty acid linoleic acid. In a more preferred aspect, the triglyceride includes three CLA residues in the form of an ester with glycerol. The CLA residues are preferably the most active isomers of CLA, such as the cis,trans-9,11 and trans,cis-9,11 isomer or the cis,cis-9,11 isomer, but may include any of the other isomers. Upon ingestion, the CLA residues may be released in the stomach of the animal by enzymatic hydrolysis through, for example, the action of a lipase. The triglycerides may be purified from plant sources as described above, may be purchased commercially or may be synthesized from glycerol and the respective fatty acids by methods known in the art. The therapeutically effective amount that is administered will be dependent on at least the factors discussed above. The amount of triglyceride that is administered may be that which provides the amount of CLA specified above. The amount of triglyceride required to achieve a specific dose will depend on the number of CLA esters or residues comprising the triglyceride and can be easily calculated by one skilled in the art. The triglyceride may be administered in similar forms as described above for CLA.

CLA may be administered to an animal with diabetes, including warm-blooded vertebrates such as mammals. The list of mammals includes, for example, humans.

Reference will now be made to specific examples illustrating the compositions and methods above. It is to be understood that the examples are provided to illustrate preferred embodiments and that no limitation to the scope of the invention is intended thereby. Data from the studies below were analyzed by ANOVA (General Linear Model, LSD) using Statistical Analysis System (SAS; Cary, N.C.) or StatView for the Macintosh (Abacus Concepts, Berkeley, Calif.).

EXAMPLE 1

Activation of Peroxisome Proliferator-Activated Receptor (PPAR) by CLA

Figure 1:
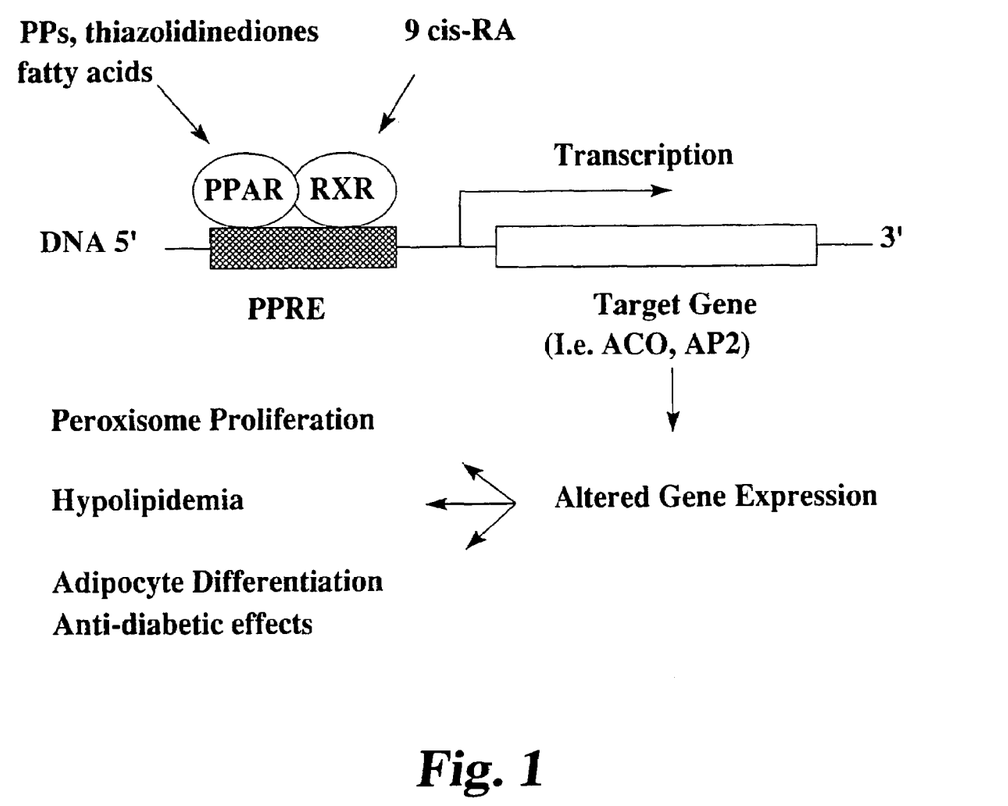
FIG. 1 shows the mechanism of action of peroxisome proliferators.

In this example, CLA is shown to be involved in the activation of several PPAR subtypes. PPAR, an intracellular protein receptor, is a member of the steroid hormone superfamily that may be important in regulating the expression of lipid metabolism enzymes and may have an effect on cell growth and/or differentiation. Three subtypes of PPAR ($\alpha$, $\beta$ and γ) have been identified in several species, including human. PPARγ is thought to be involved in the anti-diabetic and glucose lowering activity of groups of drugs known as thiazolidinediones and fibrate hypolipidemic drugs. PPAR can be activated by peroxisome proliferators, thiazolidinediones and fatty acids. The mechanism of action of peroxisome proliferators is depicted in FIG. 1 and the effects of the activators of PPAR subtypes is shown in Table 1.

TABLE 1

Activators of PPAR subtypes and their effects.

| Drug/Chemical Group | PPARα | PPARβ | PPARγ | Clinical Use or effects |
|---|---|---|---|---|
| Peroxisome proliferators | ++++ | ++ | +++ | Hypolipidemia, possible antidiabetic, hepatic peroxisome proliferation, adipocyte differentiation. |
| Long-chain fatty acids | +++ | + | ++ | Hypolipidemia, hepatic peroxisome proliferation, adipocyte differentiation |
| Thiazolidinediones | − | − | ++++ | Antidiabetic, adipocyte differentiation, decreased insulin resistance, decreased blood glucose levels |
| CLA | +++ | + | ++ | Anti-cancer effects, anti-atherogenic effects, hypolipidemia, hepatic peroxisome proliferation. Antidiabetic as shown in this disclosure |

COS-1 cells (American Type Culture Collection) were maintained in α-minimal essential media (Sigma) supplemented with 8% fetal calf serum (Gibco BRL), 0.2 mg/ml streptomycin and 200 U/ml penicillin. The pSG5-GAL4-PPAR chimera expression constructs, containing the ligand binding domain of mouse PPARα, β or γ, as well as the (UAS)$_5$-tk-CAT reporter construct were kindly provided by Steven A. Kliewer (Glaxo Research Institute). At 75–90% confluence, COS-1 cells were co-transfected with GAL4-PPAR, (UAS)$_5$-tk-CAT, and pSV-βGal (Promega) as described in Lehmann, J. M. et al., *J. Biol. Chem.* 270, 12953–12956 (1995). Twenty-four hours after transfection, the cells were treated with the indicated amounts of CLA, or a single 100 μM dose of 4-chloro-6-(2,3-xylindino)-2-pyrimidinylthio)-acetic acid (Wy 14,643; a hypolipidemic drug known as a peroxisome proliferator). After 6 hours of treatment, the cells were harvested and chloramphenicol acetyltransferase levels were assessed by ELISA (Gibco BRL) according to the manufacturer's instructions. Data is expressed relative to β-galactosidase activity. CLA used in this experiment was obtained from a commercially available mixture from NuChek Prep, Elysian Minn. The mixture contained about 41.2% by weight of a composition including cis,trans-9,11-octadecadienoic acid and trans,cis-9,11-octadecadienoic acid, about 44% by weight trans,cis-10,12-octadecadienoic acid, about 9.4% by weight cis,cis-10,12-octadecadienoic acid, about 1.3% by weight of a composition including trans,trans-9,11-octadecadienoic acid and trans,trans-10,12-octadecadienoic acid, about 1.1% by weight cis,cis-9,11-octadecadienoic acid, about 0.7% by weight linoleic acid and about 2.2% of other lipids as mentioned above.

Figure 2:
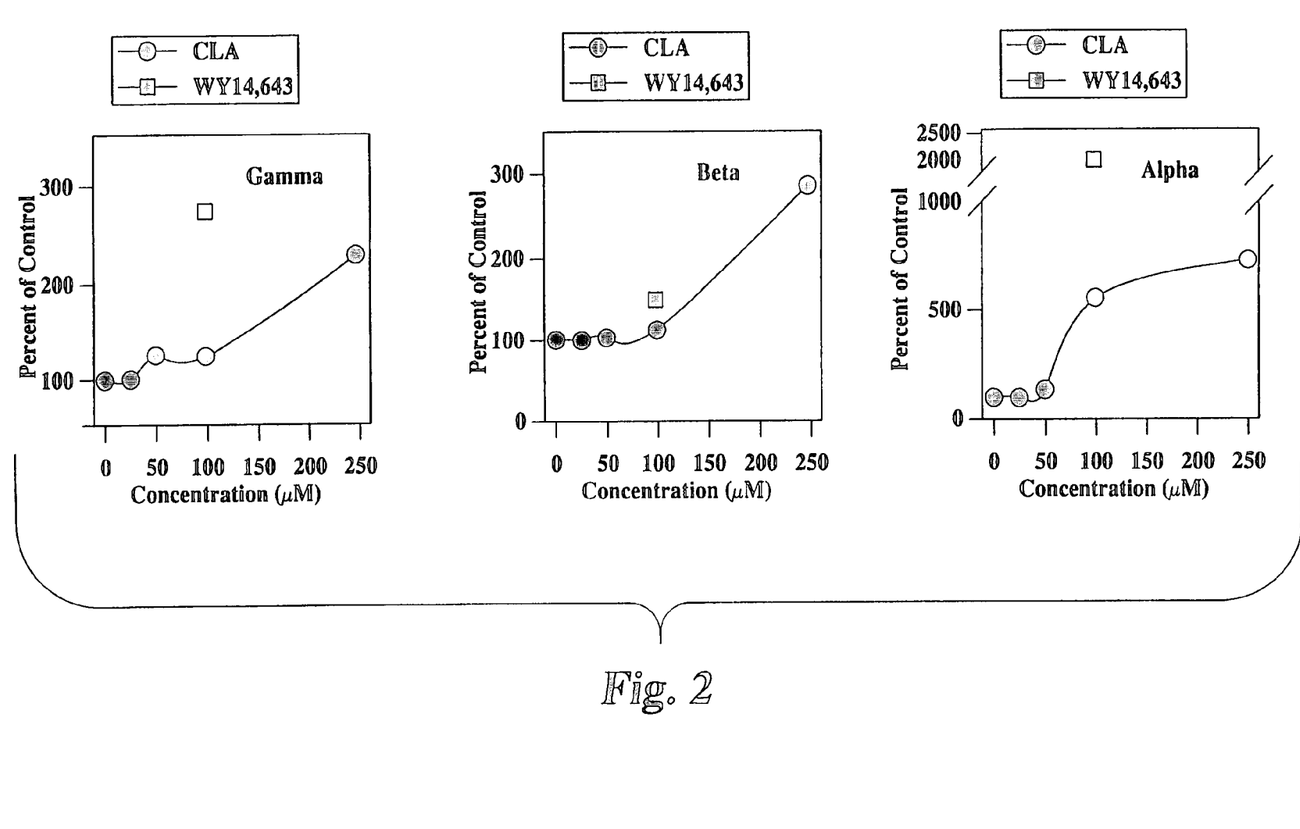
FIG. 2 depicts the biological effects of peroxisome-proliferator activated receptor (PPAR) activation by CLA.
Figure 3:
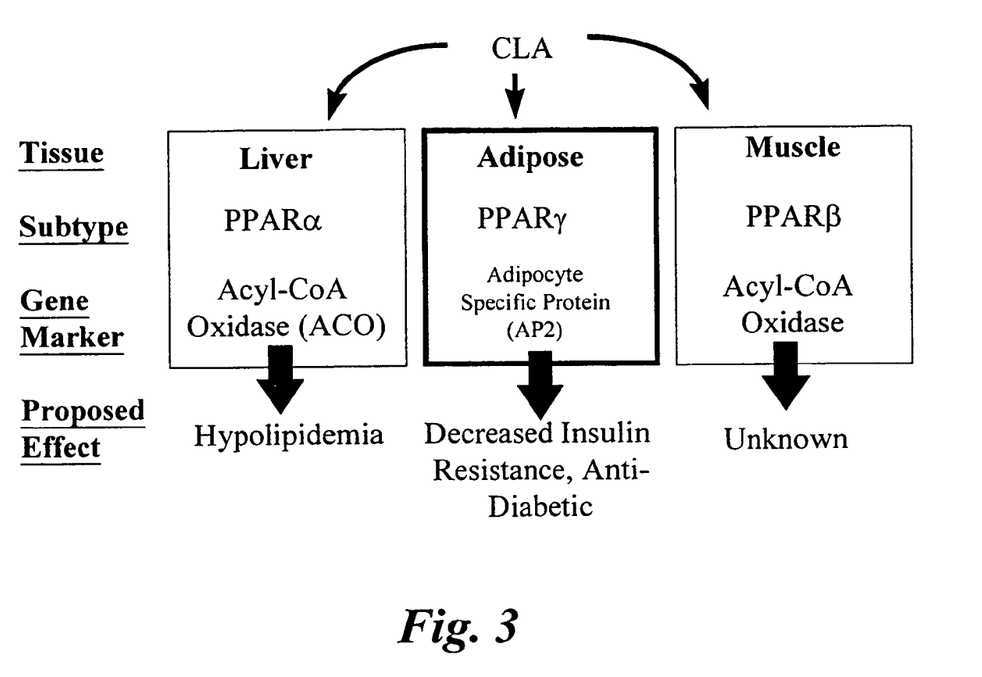
FIG. 3 depicts graphs of the amount of chloramphenicol acetyltranferase produced as a percent of control versus the concentration of CLA and 100 $\mu$M of WY 14,643 with different PPAR subtypes. Left panel, PPAR$\alpha$; Middle panel, PPAR$\beta$; Right panel, PPAR$\gamma$.

FIG. 2 shows that all subtypes of PPAR studied were activated by CLA. PPARα was activated to a greater extent than either PPARβ or PPARγ. However, PPARβ and PPARγ were activated a significant amount (approximately 2-fold more than the control value). The activation of PPARα by the commercially available mixture is believed to be the result of the cis,trans-9,11-octadecadienoic acid isomer as discussed in Example 2. Moreover, the biological effects of PPAR activation by CLA will depend on the tissue and the predominant PPAR subtype being examined as shown in FIG. 3.

EXAMPLE 2

Activation of PPAR Subtypes by CLA Isomers

In this example, certain PPAR subtypes are shown to be activated by CLA isomers. The same experimental procedure as described in Example 1 was carried out to generate the data shown in FIG. 4. However, a 100 μM concentration of selected isomers of CLA were also utilized in the transfection assay to determine whether specific isomers of CLA could activate any of the PPAR subtypes.

Figure 5:
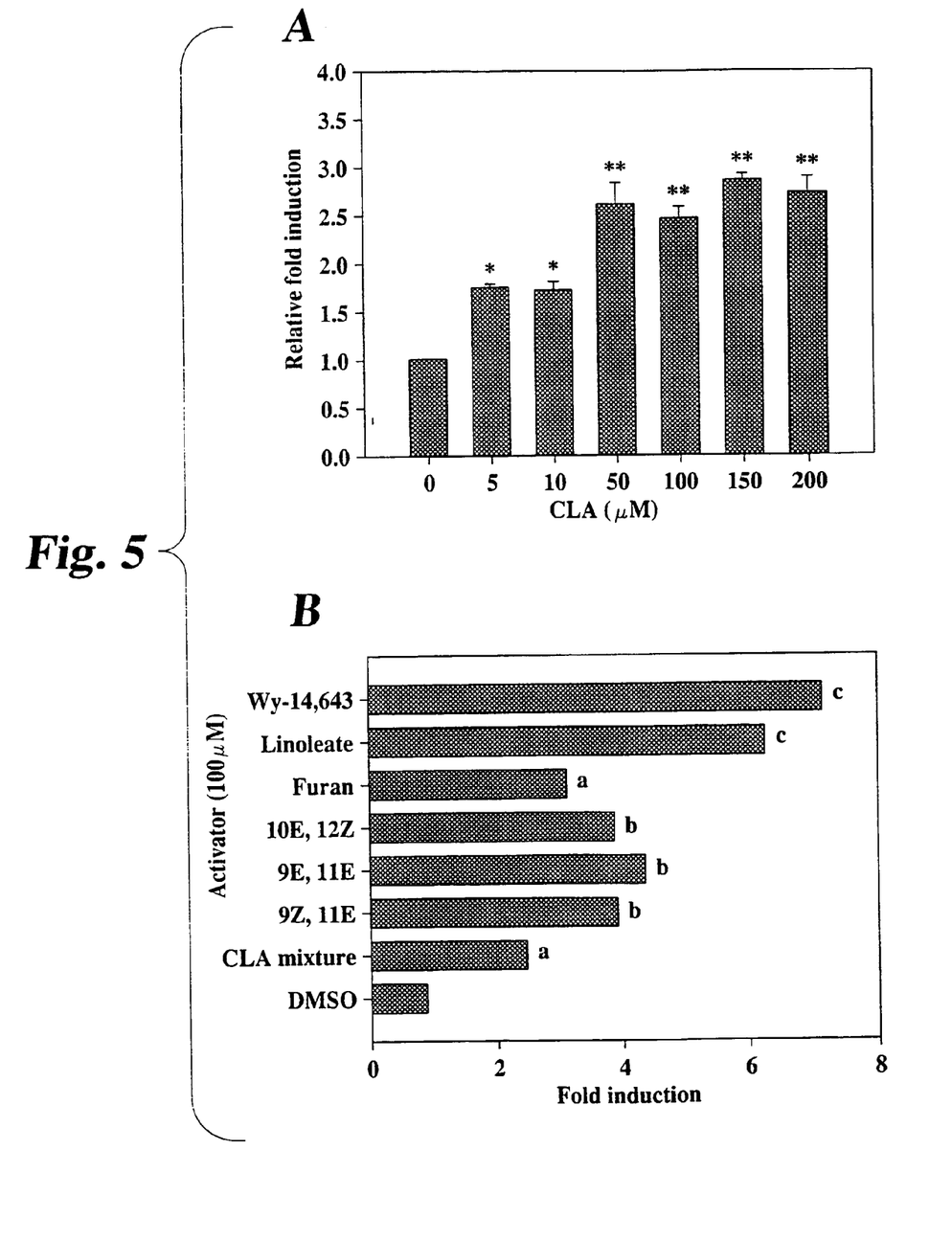
FIG. 5 represents bar graphs showing the extent that CLA and various CLA isomers activate full length PPAR$\alpha$. Panel A: shows activation of full length mouse PPAR$\alpha$ by CLA. Transfected cells were treated for six hours with increasing concentrations of a CLA mixture (0 $\mu$M, 5 $\mu$M, 10 $\mu$M, 50 $\mu$M, 100 $\mu$M, 150 $\mu$M or 200 $\mu$M). Asterisks denote values that are significantly different from DMSO treated cells ($p<0.05$, $n=3$); Panel B: shows activation of full length mPPAR$\alpha$ by different geometric isomers of CLA. Transfected cells were treated for six hours with 100 $\mu$M of each of the activators shown. Different letters denote significant differences ($p<0.05$, $n=3$).
Figure 6:
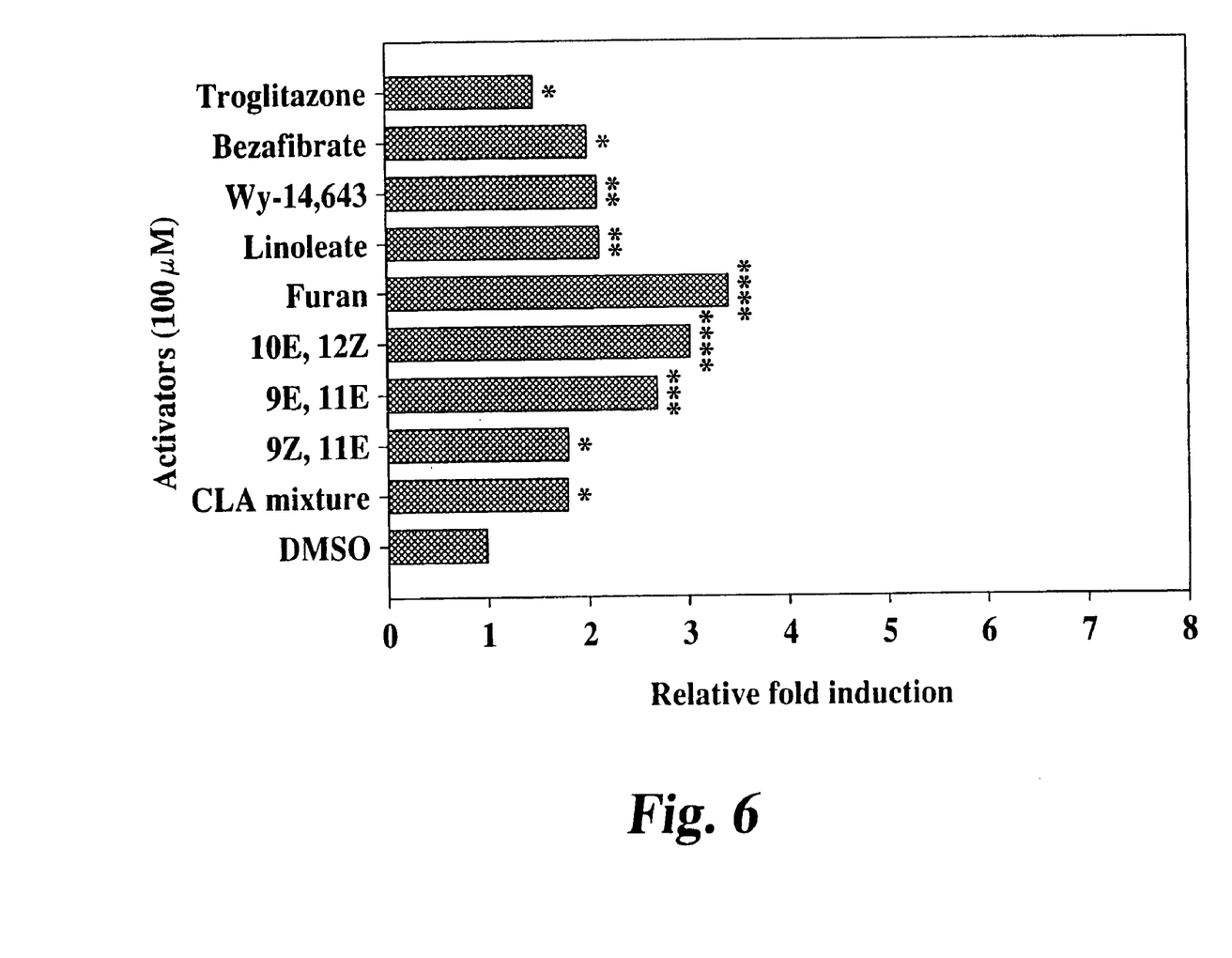
FIG. 6 represents a bar graph showing the extent that CLA and various CLA isomers activate full length mouse PPAR$\beta$. Transfected cells were treated with 100 $\mu$M of the indicated compounds. Asterisks denote significant differences ($p<0.01$, $n=3$).
Figure 7:
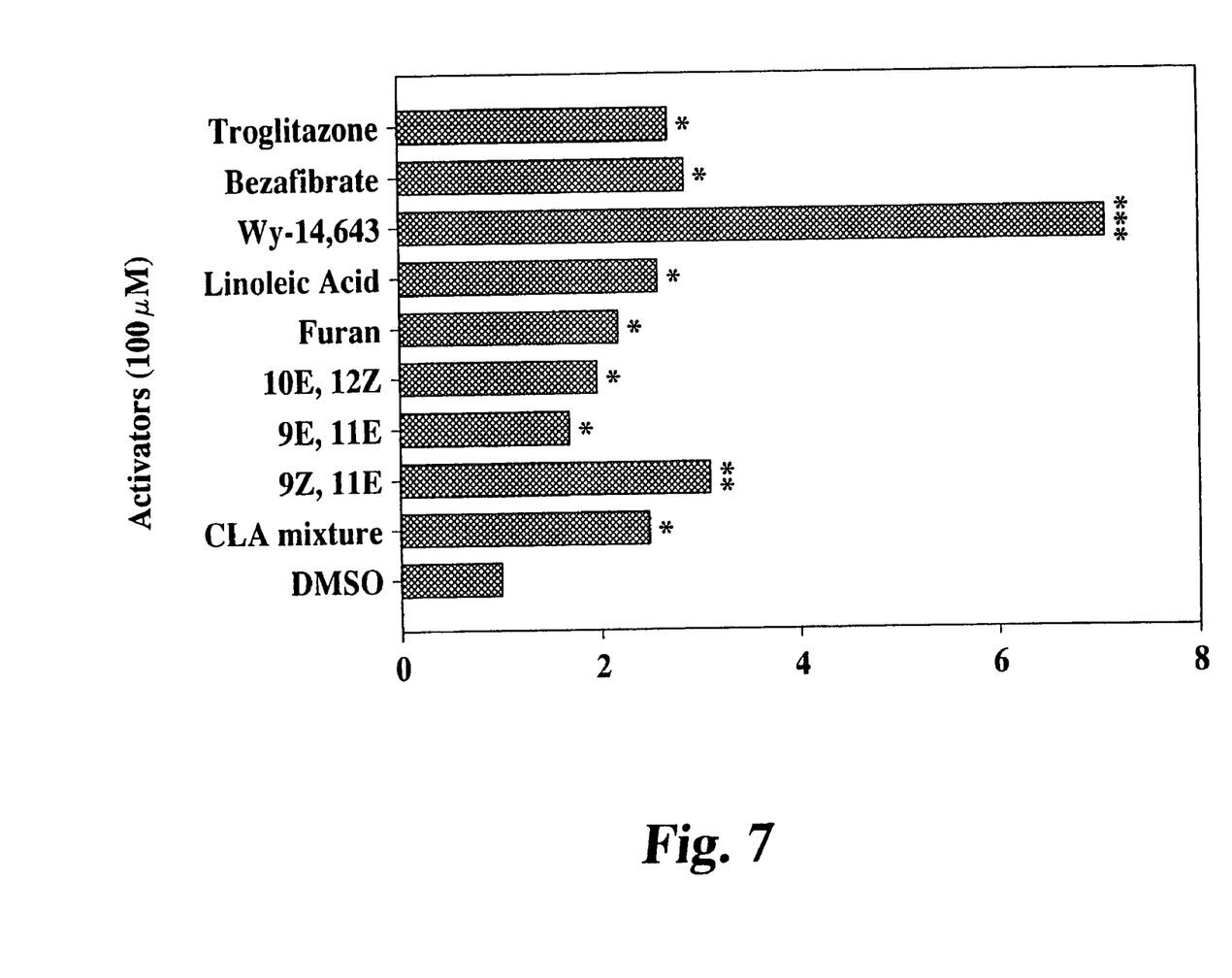
FIG. 7 represents a bar graph showing the extent that CLA and various CLA isomers activate full length mouse PPAR$\gamma$. Transfected cells were treated for six hours with 100 $\mu$M of the indicated compounds. Asterisks denote significant differences ($p<0.05$, $n=3$).

The data in FIGS. 5–7 was generated utilizing constructs including full length mouse PPARα, PPARβ or PPARγ and a luciferase reporter gene. The CV-1 cell line (African green monkey kidney cells) used was obtained from American Type Culture Collection (#CCL-70). The cells were grown in Eagle minimal essential medium containing 10% fetal bovine serum (GIBCO). For each transfection involving PPARα, 625 ng pcDNA3-PPARα expression vector was used along with 250 ng of psV-GL-2-PPRE-luciferase reporter plasmid and 250 ng of pSV-β-galactosidase internal control plasmid. For each transfection involving PPARβ or PPARγ, either 625 ng pSG5-mouse-PPARβ or 625 ng pSG5-mouse-PPARγ was used along with 250 ng of the psV-GL2-PPRE-luciferase reporter plasmid and 250 ng of pSV-β-galactosidase internal control plasmid. Cells were transfected using Lipofect AMINE™ reagent (GIBCO) and phenol red-free, serum free medium (OptiMEM®I, GIBCO Life Technologies, Grand Island, N.Y.). Seven hours post-transfection, charcoal stripped serum (Cocalico Biologicals, Inc. Reamstown, Pa.) was added to the media (10% final concentration) for an overnight incubation (16 hours). Transfected cells were treated for six hours with various doses or 100 μM of CLA, the 9Z,11E (cis,trans-9,11) isomer (97% purity), the 9E,11E (trans,trans-9,11) isomer (98% purity), the 10E,12Z (trans,cis-10,12) isomer or the other indicated activators. Luciferase and β-galactosidase activities were assayed on cell lysates following the manufacturer's protocols (Promega, Madison, Wis.). The data were quantified relative to luciferase/β-galactosidase activity expressed as a ratio to vehicle-treated cells (0.1% DMSO).

Figure 4:
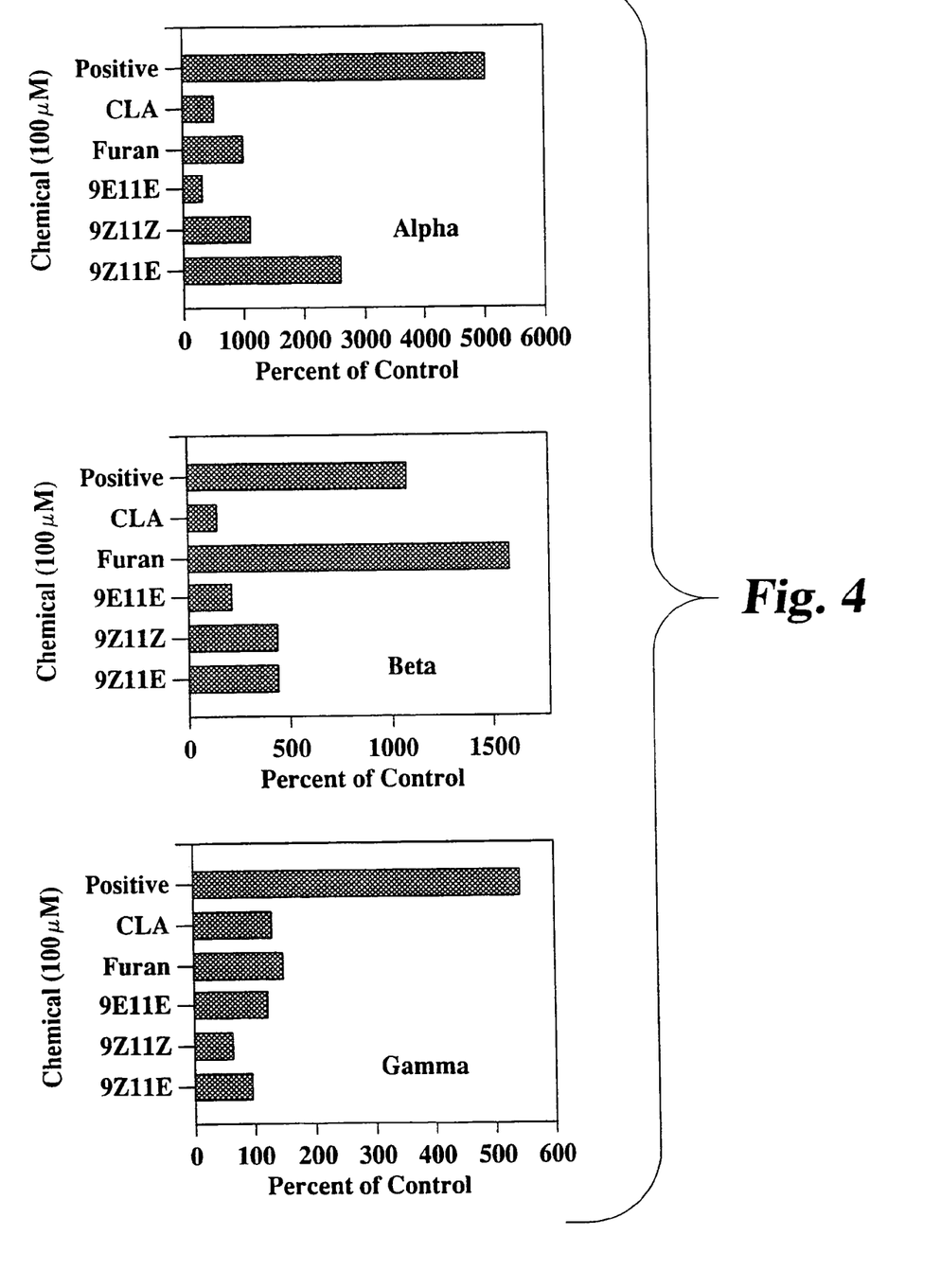
FIG. 4 represents bar graphs showing the extent that various CLA isomers activate the 3 different PPAR subtypes. All chemicals were given at 100 $\mu$M in dimethylsulfoxide (DMSO). Positive controls for PPAR$\alpha$ (Wy 14,643), PPAR$\beta$ (Bezafibrate; 2-[4-[2-[(4-chlorobenzoyl)amino]-ethyl]phenoxy]-2-methylpropanoic acid]) and PPAR$\gamma$ (Troglitazone) are shown for comparison. The furan used was 8-(5-hexyl-2-furyl)-octanoic acid which is an oxidation product of CLA. Data depicts the average of two experiments.

FIG. 4 shows that all of the isomers examined activated all of the PPAR subtypes. However, the 9Z11Z (cis,cis-9,11) and 9Z11E (cis,trans-9,11) isomers activated PPARα and PPARβ more than the CLA mixture and the 9E11E (trans,trans-9,11) isomer only activated PPARβ more than CLA mixture alone. None of the isomers activated PPARγ more than the CLA mixture. Moreover, in a similar study, human PPARγ was also activated by CLA (data not shown), showing that the molecular events underpinning the present invention are also occurring in humans.

The data shown in FIGS. 5–7 show that all of the CLA isomers tested, including the trans,cis-10,12-octadecadienoic acid isomer, activate the respective PPAR subtypes with respect to the DMSO control. Moreover, the data in FIGS. 5 and 6 further show that the trans,cis-10,12 CLA isomer activated PPARα and PPARβ significantly more than the CLA mixture alone.

EXAMPLE 3

Effect of CLA on Gene Expression

Activation of certain PPAR subtypes results in altered gene expression, such as gene induction. In this example, CLA was found to induce two markers of differentiation of mouse 3T3-L1 preadipocytes into differentiated adipocytes, which requires PPARγ activation. The two markers studied were adipocyte protein-2 (mAP2) mRNA and PPARγ mRNA.

3T3-L1 Cell Culture

Mouse 3T3-L1 preadipocytes (American Type Culture Collection) were maintained in Dulbecco's modified Eagle's medium (DMEM) supplemented with 10% fetal calf serum (Gibco BRL) 0.2 mg/ml streptomycin and 200 U/ml penicillin ("growth media"). Differentiation was induced as described by Brandes, R., Arad R., and Bar-Tana, J., *Biochem. Pharmacol.* 50, 1949–1951 (1995). Briefly, differentiation was induced by adding various concentrations of CLA (25–250 μM final concentration), linoleic acid (100 μM), Wy 14,643 (100 μM) or vehicle (DMSO) in DMEM with 10% FCS and 0.1 μM dexamethasone ("induction media") to confluent 3T3-L1 preadipocytes. After 48 hours, the induction media was removed and replaced by induction media with 4 mU/ml insulin. This media was changed every 48 hours. At various time intervals, the cells were rinsed twice with PBS and total RNA extracted using TriReagent (Molecular Research Center).

The differentiation of mouse 3T3-L1 cells was monitored by examining adipocyte-specific markers including PPARγ (γ1 and γ2) and adipocyte protein-2 (mAP2). The housekeeping gene β-actin was also examined as described in Vanden Heuvel, J. P. et al., *Cancer Res.* 54, 62–68 (1994). Quantitative reverse transcriptase polymerase chain reaction was utilized to determine mRNA expression for these genes (as described in Vanden Heuvel, J. P., *PCR Applications in Molecular Toxicology,* 218 pgs. CRC Press, Boca Raton, Fla. (1997), see Table 2 for primer sequences utilized) using internal standards specific for each primer set (as described in Vanden Heuvel, J. P., Tyson, F. and Bell, D. A., *Biotechniques* 14, 395–398 (1993)).

Figure 8:
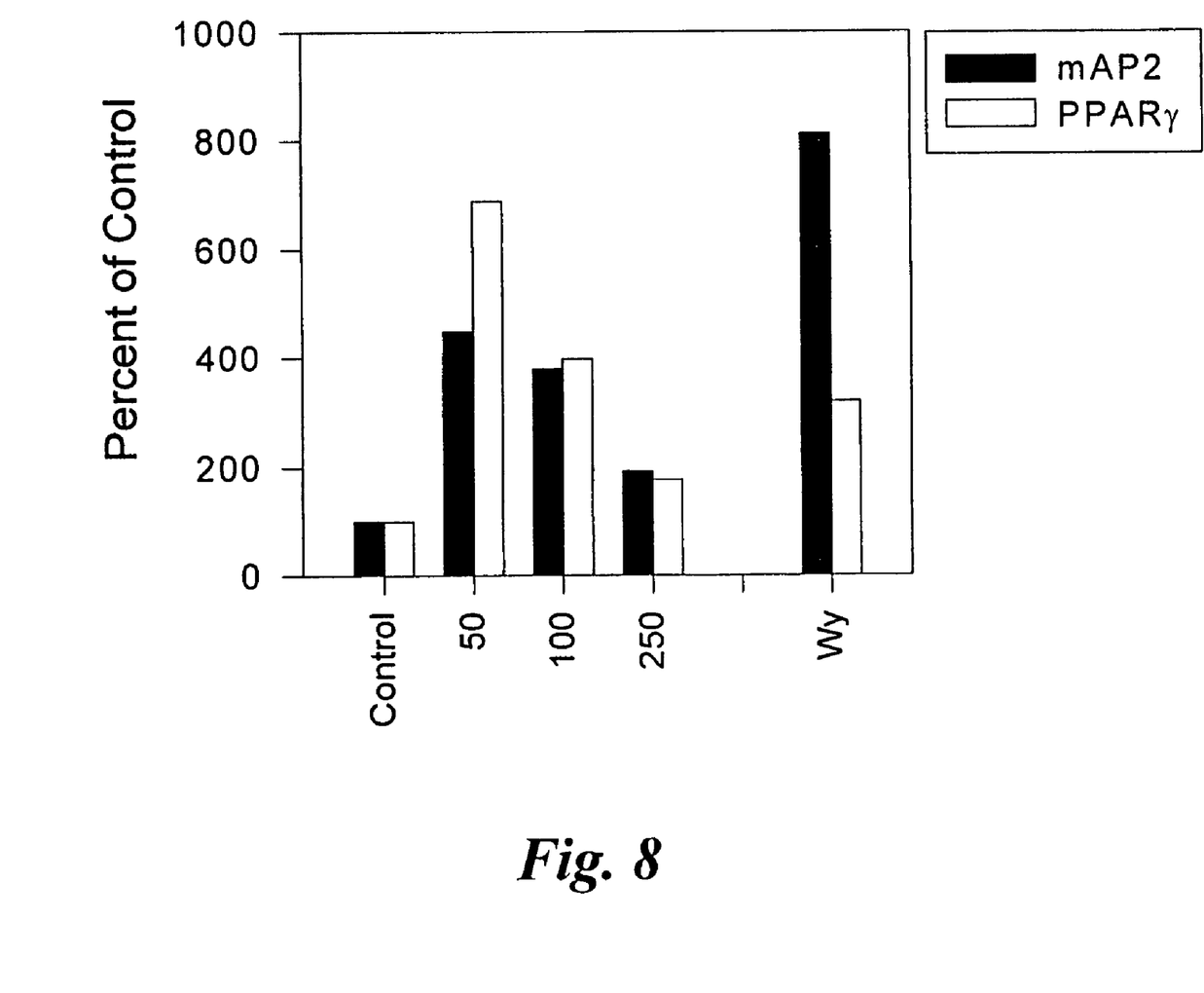
FIG. 8 depicts a bar graph showing the effects of CLA on markers of differentiation in 3T3-L1 preadipocytes. Mouse preadipoctye cells were treated at confluence for 48 hours with induction media which contains the indicated concentrations of CLA, 100 $\mu$M Wy 14,643 (Wy) or vehicle (DMSO). Induction media with insulin was subsequently added to the cells. Quantitative RT-PCR was performed using internal standards specific for each gene. The data is expressed as the average of three samples as a percent of DMSO treated cells correcting for $\beta$-actin expression.

As seen in FIG. 8, CLA is effective at inducing both mAP2 and PPARγ mRNA. It is also seen that CLA is more potent as a PPARγ ligand in the 3T3-L1 bio-assay than would nave been expected from the transactivation assays, the results of which are depicted in FIG. 4. FIG. 8 also shows that the most effective concentration of CLA in the differentiation assay was 50 μM.

Animal Studies

Male Zucker fatty (fa/fa) rats and lean littermates (wt) were obtained at six weeks of age from Genetic Models, Inc. (Indianapolis, Ind.). Because the primary aim of the study was to determine the ability of CLA to improve insulin action and prevent the onset of diabetes, all rats were determined normoglycemic prior to assignment to experimental treatments. (The diets are discussed in the subsequent section). After maintaining rats on experimental diets for 14 days, rats were euthanized by $CO_2$ and cervical dislocation and tissues collected, weighed and frozen. RT-PCR was performed as described above.

The genes utilized as markers of tissue and subtype specific PPAR activation included Acyl-CoA Oxidase (ACO; found in the liver and induced by PPARα activation), Adipocyte Specific Protein (mAP2; found in adipose tissue and induced by activation of PPARγ) and ACO in the muscle (induced by PPARβ).

Figure 9:
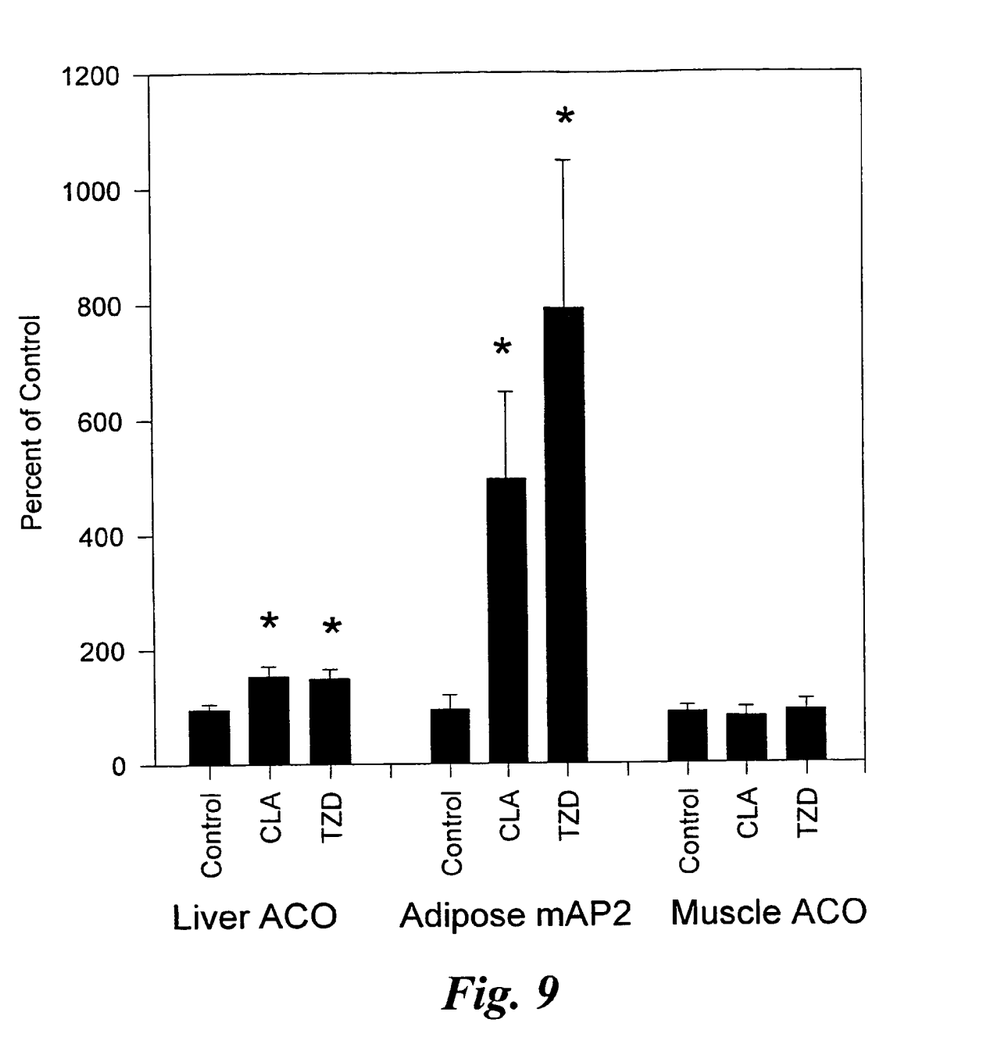
FIG. 9 depicts a bar graph showing the effects of CLA and troglitazone (TZD) on tissue-specific gene expression. ACO and mAP2 were quantitated by RT-PCR. Asterisks denote a statistically significant difference from the rats fed the control diet ($P<0.05$).

As seen in FIG. 9, both CLA and Troglitazone (5-[[4-[3, 4-Dihydro-6-hydroxy-2,5,-7,8-tetramethyl-2H-1-benzopyran-2-yl)methoxy]phenyl]methyl]-2,4-thiazolidinedione; TZD; Rezulin, Parke-Davis) significantly induce ACO mRNA expression in the PPARα-containing tissue (liver) and a tissue with predominantly PPARγ (adipose tissue) but had no effect on a tissue with predominantly PPARβ (muscle). The induction of mAP2 in adipose tissue verifies the PPARγ activation observed in the 3T3-L1 cells.

EXAMPLE 4

Effect of Dietary CLA on Normalizing Glucose Tolerance in the Zucker Fatty fa/fa Rat The Zucker fa/fa rats are an excellent animal model for the examination of adult onset diabetes. In this example, the effect of three different diets (control, CLA, TZD) on the levels of circulating insulin, triglycerides and free fatty acids in the fa/fa rats as well as their lean counterparts (wildtype, wt) were determined. Moreover, to determine if CLA

TABLE 2

Sequence of primers utilized in RT-PCR

| Primer | Sequence | Length of Product (bp) | |
|---|---|---|---|
| | | Target | Int. Std.* |
| mAP2 forward | 5' ACT GTG GCC TGA CCC ACT TCT ATG | 190 | 314 |
| mAP2 reverse | 5' AGG GGG CTT CTG GCA AAC AAT | | |
| mPPARγ forward | 5' TGC TGG CCT CCC TGA TGA ATA | 315 | 352 |
| mPPARγ reverse | 5' TTG CCC AAC AGC TGA GAG GAC | | |
| Actin forward | 5' CCT CTA TGC CAA CAC ACT | 125 | 153 |
| Actin reverse | 5' ACC CAC CAA TCC ACA CAG | | |
| ACO forward | 5' ATT CGG TGT TGT AAG TGC | 417 | 340 |
| ACO reverse | 5' TTG CTC CCT CCC TCT TCA | | |

*An internal standard was synthesized only for genes that were to be quantitated increases insulin sensitivity as a PPARγ activator, such as TZD, a glucose tolerance test was performed.

Diet components were obtained from Dyets, Inc. (Bethlehem, Pa.) and the CLA isomeric mixture (90% pure mixture) from PharmaNutrients, Chicago, Ill. The CLA mixture had the following isomeric distribution: 42% of a composition including cis,trans-9,11 and trans,cis-9,11-octadecadienoic acid; 43.5% trans,cis-10,12-octadecadienoic acid; 1% cis,cis-9,11-octadecadienoic acid; 1% cis,cis-10,12-octadecadienoic acid; and 1.5% of a composition including trans,trans-9,11-octadecadienoic acid and trans,trans-10,12-octadecadienoic acid, all on a weight percent basis. The CLA mixture also included, on a weight percent basis, about 0.5% linoleate, about 5.5% oleate and about 5% other lipids as discussed above. The thiazolidinedione, TZD (Rezulin™, Parke-Davis, Ann Arbor, MI), was used as a positive control for anti-diabetic activity in these studies. Male Zucker fatty (fa/fa) rats and lean littermates (wt) were obtained at six weeks of age from Genetic Models, Inc. (Indianapolis, Ind.). Because the primary aim of the study was to determine the ability of CLA to improve insulin action and prevent the onset of diabetes, all rats were determined normoglycemic prior to assignment to experimental treatments. After maintaining rats on experimental diets for 14 days, rats were euthanized by $CO_2$ and cervical dislocation and blood collected and immediately analyzed for post-prandial glucose concentrations (see below) or placed into heparinized test tubes for plasma analyses as described below. Epididymal fat pads and livers were harvested and weighed. An aliquot of the epididymal fat pad was isolated into buffered saline for glucose transport analyses and the remaining epididymal fat pad and gastrocnemius muscle were isolated, immediately frozen in liquid nitrogen and stored at −80° C. until mRNA and protein analyses were performed.

Experimental Diets

Three isocaloric, experimental diets were formulated according to a modified AIN-76 mixture containing 6.5% (by weight) fat (diet described in American Institute of Nutrition: Report of the American Institute of Nutrition Ad Hoc Committee on Standards for Nutritional Studies, *J. Nutr.* 107 1340–1348 (1977) but includes 6.5% by weight fat instead of 5% by weight fat). The same amount of corn oil (5%) was used in all diets since corn oil is rich in linoleic acid, an essential fatty acid. The diets contained either 5% corn oil+1.5% lard+no CLA (Control Diet), 5% corn oil+1.5% CLA (CLA Diet), or 5% corn oil+1.5% lard+0.2% troglitazone (TZD Diet). A dose of 1.5% CLA was chosen based on previous studies in our laboratory showing this dose to modulate PPAR-associated gene expression in the liver (Belury, M. A. et al., *Nutr. Biochem.* 8:579–84 (1997)) and inhibit tumorigenesis in murine skin (as shown in Belury, M. A. et al., *Nutr. Cancer* 26, 149–157 (1996)). The dose of TZD (0.2%) used in this study has been shown to be effective at normalizing glucose tolerance after 15 days and suppressing elevated glucose, triglycerides, free fatty acids and urinary protein in Zucker (fa/fa) rats. Diets were fed on alternate days and rats were allowed free access to food and water. Body weights were measured twice weekly and average food consumption estimated by measuring differences in weight of freshly supplied diet and diet remaining in feeders two days later. Taking into account the average body weight of the fa/fa rats and the amount of food they consumed, the fa/fa rats received a daily dose of about 1.71 mg CLA/kg body weight, which amounted to a daily dose of about 375 mg.

Glucose Tolerance Tests

In order to compare the effects of CLA and TZD on insulin action, a glucose tolerance test was conducted on day 11 of dietary intervention. Animals were fasted overnight (16 hours). Conscious rats were injected intraperitoneally with D-glucose (1 g/kg body weight) and blood samples were collected via the tail vein prior to the injection (time 0) and at 2, 5, 10, 15, 20, 40, 60, 120 and 180 minutes following injection.

Determination of Blood Metabolite and Hormone Concentrations

Blood glucose levels were determined using a One Touch glucose meter (Lifescan, Inc.). Plasma insulin levels were determined using commercially available radioimmunoassay kits (Linco Research, St. Charles, Mo.). Plasma nonesterified fatty acids were quantified using a calorimetric kit (Wako). Plasma triglyceride concentrations were determined using a commercially available kit (Sigma Diagnostics, St. Louis, Mo.).

Figure 10:
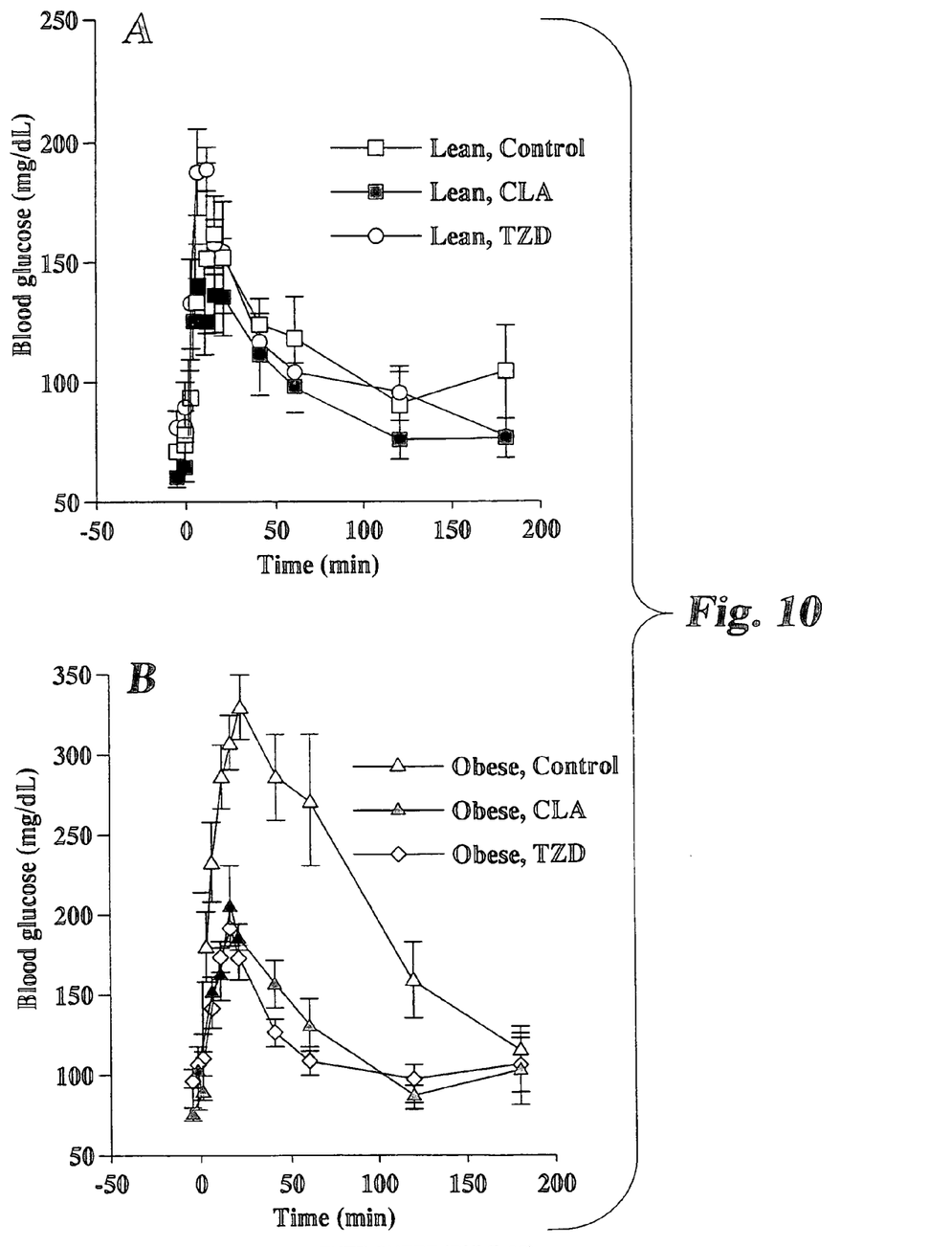
FIG. 10 represents graphs showing the effect of dietary CLA on glucose tolerance. Zucker lean (Panel A) or fa/fa (obese, Panel B) rats were fed experimental diets for 14 days and glucose tolerance was measured. Values represent mean glucose (mg/dl)±S.D. (n=4 lean rats or 8 fa/fa rats).

FIG. 10 depicts the results of the glucose tolerance test. As expected, a decreased ability to remove glucose from the blood is seen in the fa/fa rats (compare lean control versus obese control). In the fa/fa rats fed either CLA or TZD, blood glucose was reduced much more rapidly than the respective control animals. As glucose tolerance is the predominant test used to assess the existence of non-insulin-dependent diabetes mellitus (NIDDM), the data depicted in FIG. 10 convincingly show that CLA is as effective as TZD for improving glucose tolerance. Therefore, CLA may be an effective treatment for individuals with NIDDM.

The results showing the relative levels of circulating insulin, plasma triglycerides and circulating free fatty acids are shown in Table 3.

TABLE 3

Effect of Dietary CLA on Glucose, Triglyceride and Free Fatty Acid Concentrations in Zucker Rats*

| Diet | Insulin (ng/dl) ± S.D. | Plasma Triglycerides (mg/dl) ± S.D. | Free Fatty Acids (mMol) + S.D. |
| --- | --- | --- | --- |
| wt, Control | 2.8 ± 0.1[a] | 92.1 ± 16.7[bc] | 1.651 + 0.497[ab] |
| wt, CLA | 2.8 ± 0.5[a] | 66.2 ± 18.0[bc] | 1.170 + 0.335[bc] |
| wt,TZD | 1.4 ± 0.1[a] | 61.1 ± 12.1[c] | 1.139 + 0.277[c] |
| fa/fa, Control | 38.9 ± 2.8[b] | 408.3 ± 148.7[a] | 1.959 + 0.402[a] |
| fa/fa, CLA | 20.6 ± 3.3[c] | 149.4 ± 78.4[b] | 1.004 + 0.262[c] |
| fa/fa,TZD | 5.6 ± 0.5[d] | 57.08 ± 12.3[c] | 0.778 + 0.378[c] |

Plasma insulin triglycerides and free fatty acid concentrations were measured in fed rats after experimental diets were fed for 14 days.
[a–d]Values (± S.D.) with significant differences (p < 0.05) within columns are denoted by different superscripts.

As expected, the fa/fa rats exhibited higher plasma insulin and triglycerides compared to wt animals. However, CLA significantly improved symptoms of diabetes causing a 50–60% decline in plasma insulin, triglycerides and free fatty acids. Moreover, TZD markedly decreased circulating insulin, triglycerides and free fatty acids in the fa/fa rats, thus verifying TZD as an effective anti-diabetic agent. For additional information on the normalization of glucose tolerance and other biological effects using CLA, reference may be made to Biochem. Biophys. Res. Comm., 244, 678–682 (1998).

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected. In addition, all references cited herein are indicative of the level of skill in the art and are hereby incorporated by reference in their entirety.

What is claimed is:

1. A method of treating type II diabetes mellitus symptoms of glucose intolerance and elevated plasma insulin in an animal, said method comprising administering to said animal a therapeutically effective amount of conjugated linoleic acid, said method producing enhanced glucose tolerance and reduced plasma insulin levels in said animal.

2. The method of claim 1, wherein said conjugated linoleic acid is administered orally.

3. The method of claim 2, wherein said conjugated linoleic acid is administered in a unit dosage form.

4. The method of claim 3, wherein said unit dosage form is a food product.

5. The method of claim 1, wherein said conjugated linoleic acid is selected from the group consisting of 9,11-octadecadienoic acid, esters thereof, geometric isomers thereof, salts thereof and mixtures thereof.

6. The method of claim 5, wherein said geometric isomers have configurations selected from the group consisting of trans,trans; cis,cis; trans,cis; and cis,trans.

7. The method of claim 1, wherein said conjugated linoleic acid is selected from the group consisting of 10,12-octadecadienoic acid, esters thereof, geometric isomers thereof, salts thereof and mixtures thereof.

8. The method of claim 7, wherein said geometric isomers have configurations selected from the group consisting of trans,trans; cis,cis; trans,cis; and cis,trans.

9. The method of claim 1, wherein said conjugated linoleic acid is comprised predominantly of cis,trans-9,11-octadecadienoic acid and trans,cis-octadecadienoic acid.

10. The method of claim 1, wherein said conjugated linoleic acid is comprised predominantly of cis,cis-9,11-octadecadienoic acid.

11. The method of claim 1, wherein said conjugated linoleic acid is administered in an amount of about 1 mg of said conjugated linoleic acid/kg body weight to about 10,000 mg of said conjugated linoleic acid/kg body weight.

12. The method of claim 1, wherein said animal is a mammal.

13. The method of claim 12, wherein said mammal is a human.

14. The method of claim 1, wherein said conjugated linoleic acid is administered in a pharmaceutically acceptable carrier medium.

15. The method of claim 14, wherein said pharmaceutically acceptable carrier medium includes water.

16. A method of treating symptoms of glucose intolerance and elevated plasma insulin in a human with type II diabetes mellitus comprising:
   a) providing
      i) a therapeutically effective amount of conjugated linoleic acid; and
      ii) a human patient with type II diabetes mellitus; and
   b) administering said therapeutically effective amount of conjugated linoleic acid to said human diabetic patient under conditions such that said symptoms are treated by normalizing glucose tolerance and reducing plasma insulin and glucose levels.

17. The method of claim 1 wherein said symptoms further includes elevated glucose levels.

18. The method of claim 16 wherein said symptoms further includes elevated glucose levels.

* * * * *